(12) United States Patent
Storz et al.

(10) Patent No.: US 6,210,418 B1
(45) Date of Patent: *Apr. 3, 2001

(54) INSTRUMENT FOR USE IN ENDOSCOPIC SURGERY

(75) Inventors: Karl Storz, deceased, late of Tuttlingen (DE), by Sybill Storz-Reling, executor; Alfred Cuschieri, Dundee (GB)

(73) Assignee: Karl Storz GmbH & Co. KG (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/732,460

(22) PCT Filed: May 4, 1995

(86) PCT No.: PCT/DE95/00577

§ 371 Date: Apr. 3, 1997

§ 102(e) Date: Apr. 3, 1997

(87) PCT Pub. No.: WO95/30376

PCT Pub. Date: Nov. 16, 1995

(30) Foreign Application Priority Data

May 4, 1995 (DE) .................................. 44 15 521

(51) Int. Cl.[7] .................................................. A61B 17/00
(52) U.S. Cl. .......................... 606/142; 606/151; 606/158; 606/205; 600/104
(58) Field of Search .............................. 606/142, 41, 151, 606/158, 205, 210, 206, 207, 208, 211; 600/104, 106, 129, 218

(56) References Cited

U.S. PATENT DOCUMENTS 5,304,183 * 4/1994 Gourlay et al. ...................... 606/142

FOREIGN PATENT DOCUMENTS

3044186 * 11/1980 (DE) .

* cited by examiner

*Primary Examiner*—John P. Leubecker
(74) *Attorney, Agent, or Firm*—St. Onge Steward Johnston & Reens LLC

(57) ABSTRACT

An instrument for use in endoscopic surgery in human or animal bodies, said instrument, in particular, being insertable into said body through a channel of an insertion instrument.

The invented instrument is distinguished by the instrument comprising at least one operating element disposed at the distal end thereof and one oblong introduction and control component connecting in the operating element to the proximal region, and the operating element and the introduction and control component being joined in such a manner via a connecting mechanism that the operating element can be disconnected intracorporally from the introduction and control component and can be reconnected thereto.

18 Claims, 3 Drawing Sheets

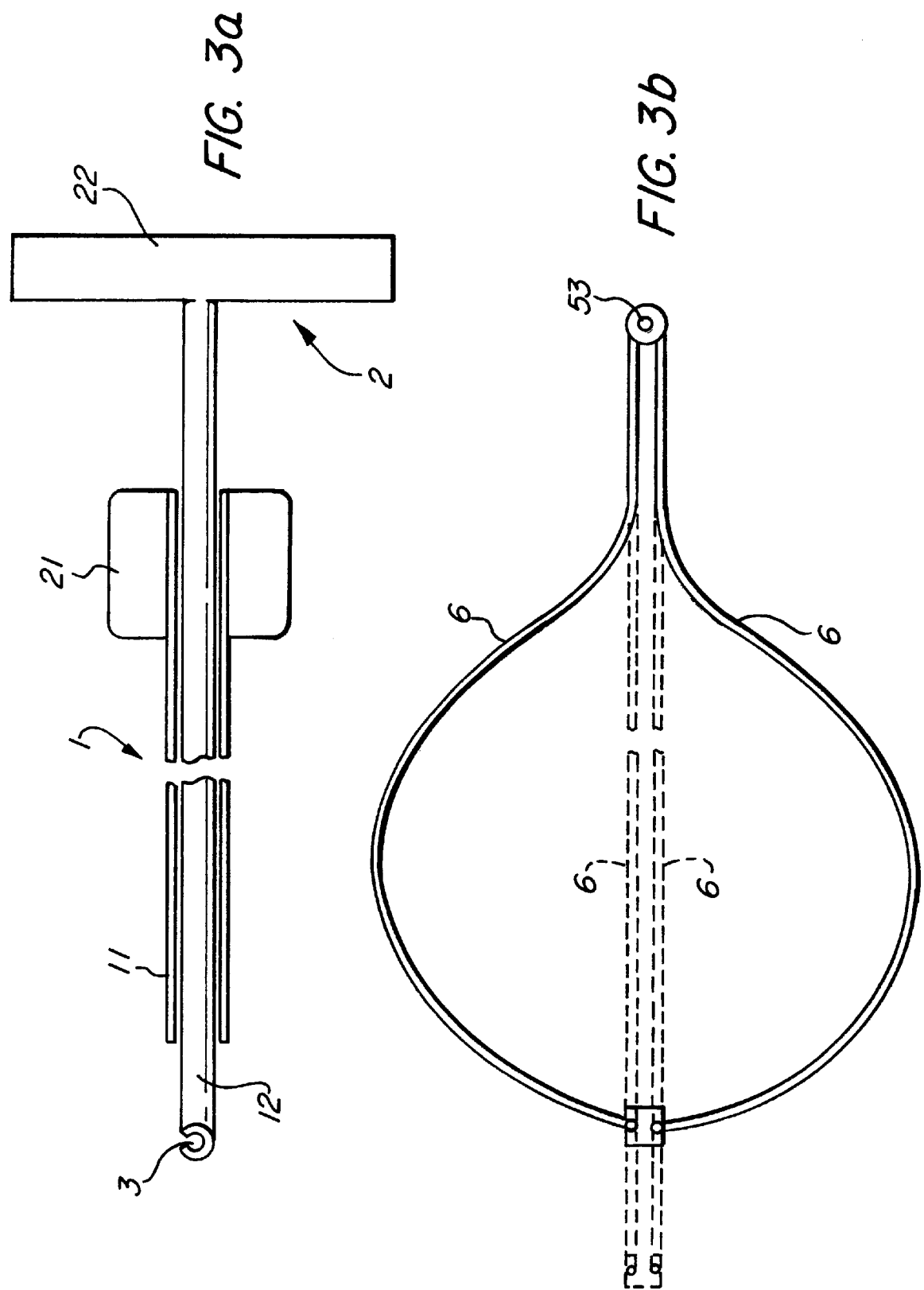

INSTRUMENT FOR USE IN ENDOSCOPIC SURGERY

TECHNICAL FIELD

The present invention relates to an instrument for use in endoscopic surgery in human and animal bodies.

In recent years, endoscopic surgery has increasingly replaced "open surgery". The actual operating instruments, such as endoscopes, tongs, scissors, etc., are introduced into the body through a channel of a charging instrument, by way of illustration, an operating trocar.

STATE OF THE ART

In some endoscopic surgery so-called tube shaft instruments, such as tongs, scissors, clip applicators, etc., are inserted into the channel of a trocar in order to conduct the respective surgical procedure. For a number of operations, trocars are employed having a channel with an interior diameter of only about 5 mm. It, therefore, is usually impossible to insert two instruments into the trocar channel simultaneously. Consequently, when using conventional endoscopic instruments, additional access has to be found if, by way of illustration, a clamp needs to be used to cut off peripheral arteries during a surgical procedure.

DESCRIPTION OF THE INVENTION

The object of the present invention is to create an instrument for use in endoscopic surgery in the body of a human or an animal in such a manner that this instrument carrying out a specific task during in-patient surgery does not require an additional access to the cavity in the human or animal body in which the surgery is conducted.

An invented solution to this object is set forth in claim 1. An element of the present invention is that the instrument is composed of at least one distally disposed operating element and an oblong introduction and control component that connects the operating element to the proximal region. The operating element and the introduction and control component are connected via a connecting mechanism in such a manner that the operating element can be disconnected intracorporally from the introduction and control component and can be reconnected to it.

In this way it is possible to first insert the operating element of the invented instrument, by way of illustration through the trocar channel serving as the insertion instrument, to position the operating element inside the body and subsequently disconnect the introduction and control component from the operating element. The introduction and control component can then be removed from the trocar channel in such a manner that an additional operating instrument, such as by way of illustration a pair of tongs or a pair of scissors or an endoscope can be inserted. After conclusion of the work with the additional operating element and after fulfillment of the function of the operating element inserted inside the body, the operating element is reconnected to the introduction and control component and removed from inside the body. However, the operating element can, of course, also be repositioned inside the body after reconnection to the introduction and control component and therefore be reused at a different site.

In this event, it is preferred if the operating element remains in at least one function state after separation from the introduction and control component. If, by way of illustration, the distal part of the instrument is a clamp, which is closed in the non-operative state, the clamp can be inserted and positioned before commencing the actual surgical procedure in such a manner that it, e.g., "cuts off" a peripheral artery. In this case, it is preferred if the clamp is designed like a bulldog clamp, like those used in open surgery. The clamp can be removed again after termination of the actual surgical procedure.

The distal part of the invented instrument, i.e. the operating element can, of course, be designed not solely as a clamp. But rather a great variety of instruments, like those known for conducting in-patient procedures during surgery, can be employed as the operating element. By way of illustration, the distal part can be a retainer or a retractor, e.g. a liver retractor.

A liver retractor is composed of a "wire cage" which "opens" after insertion of the instrument into the cavity. The retractor is closed by drawing in the introduction component.

Of course, operating elements can also be employed which can assume at least two stable function states after separation from the introduction and control component. Operating elements of this type can, by way of illustration, have the function state "active" and "passive". In order to convey the operating element from a passive to an active state without active adjustment elements, such as by way of illustration electro-mechanic elements, a preferred embodiment of the operating element has at least one adjustment element composed of a material having form memory. Moreover, super-elastic materials, etc. can also be utilized.

Furthermore, it its preferred if the connecting mechanism can transfer at least axial tensile and pressure forces to the operating element, because most of the functions of conventional operating elements can be controlled thereby and, in particular, simple conveyance of the elements to the respective desired function state is possible.

The embodiment according to which the connecting mechanism is provided with a safeguard against accidental disconnection ensures that the operating element does not accidentally get lost inside the body.

Moreover, it is preferred if the introduction and control component is composed of a rod-shaped component, which can be inserted into the channel of the insertion instrument, and a proximal operator component. In this way, the invented instrument has the same basic construction as conventional instruments, thus the operator does not have to "relearn" for operation. The proximal operator component can be disconnected from the rod-shaped component in a known manner as is known from the Karl Storz & Co "Take apart" instruments. In this way not only cleaning is simplified, but other operator components, by way of illustration, handles of different shape can also be attached if a user does not "like" a specific handle.

Furthermore, the operating element can be made rigid by withdrawal into the introduction component simplifying in this way the insertion and removal procedure and, moreover, reducing the risk of the operating element getting lost.

The connecting mechanism joining the operating element and the introduction and control component in a disconnectable manner can be designed in a great variety of ways:

For example, the connecting mechanism can be provided with a pair of tongs disposed on the introduction and control component. The jaws of these tongs can be opened and closed by operating the operator component and the tong elements have the same toothing as the gripping surfaces of the operating element.In this way, it is ensured that the tongs grip the operating element in a "non-slipping and non-turning" manner. The toothing can, in particular, be designed as squares the individual teeth of which are designed by way of illustration pyramid-shaped.

In an alternative, the operating element is connected via a hook-and-eye connection to an introduction and control component. The introduction and control component can, in this case, comprise a cylindrical tube and a rod, being movable inside the tube in direction of its longitudinal axis and bearing the hook at its distal end.

Designing the hook-and-eye connection like a keyhole connection ensures that the connection does not disconnect accidentally.

BRIEF DESCRIPTION OF THE DRAWING

The present invention is made more apparent by way of example in the following, without the intention of limiting the scope or spirit of the overall inventive idea, using preferred embodiments with reference to the accompanying drawing to which reference is explicitly made for the disclosure of all the invented details not explained more closely herein.

FIG. 3a shows the introduction component of a second preferred embodiment, and

FIG. 3b shows the distal part of the second preferred embodiment.

DESCRIPTION OF PREFERRED EMBODIMENTS

In the first preferred embodiment shown in FIG. 1, the operating element of the instrument is a clamp, which is closed when not in the operated state and which, in particular, is designed as a kind of bulldog clamp.

Figure 1A:
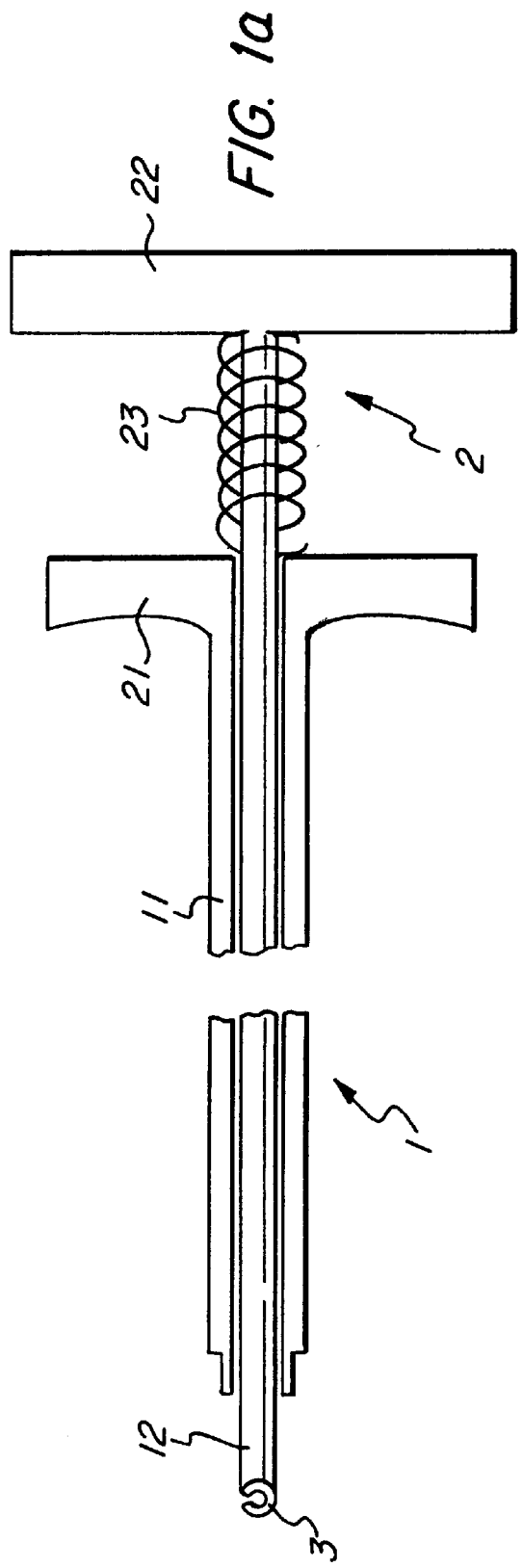
FIG. 1a shows the introduction component of a first preferred embodiment.

The introduction and control component shown in FIG. 1a is composed of a rod-shaped component 1, which can be inserted into the channel of a not depicted insertion instrument, such as a trocar, and a proximal operator component 2. The rod-shaped part 1, for its part, is composed of a cylindrical tube 11 and a rod 12, which can be moved in the tube 11 in the direction of its longitudinal axis, and which bears on its distal end a hook 3, the purpose of which is to connect the introduction component to the distal end. The operator component 2 is composed of two handles 21 and 22 of which handle 21 is connected to tube 11 and handle 22 is connected to rod 12. A spring 23 is inserted between the handles 21 and 22.

Figure 1B:
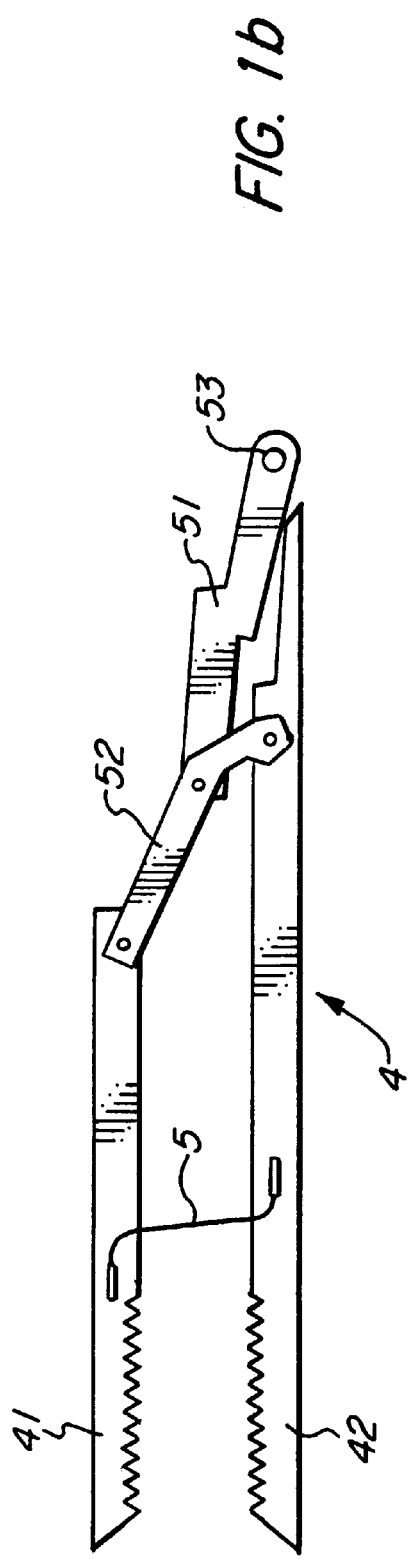
FIG. 1b shows the distal part of the first preferred embodiment.

FIG. 1b shows the clamp 4, which forms the distal end of the instrument and which is designed like the, as such known, bulldog clamp. In a clamp of this type, spring 5 pretensions the jaw components 41 and 42 in such a manner that the jaw components 41 and 42 are closed in the non-operated state and pretensioned in such a manner that they can, by way of illustration, cut-off an artery. By moving the rod 12, the hook 3 of which engages in an eye 53 on the clamp, the jaws of clamp 4 can be opened via the elements 51 and 52. The hook-and-eye connection is designed like a keyhole connection in such a manner that the connection can only be disconnected in a specific position and therefore accidental disconnection is impossible.

In order to attach the clamp, the instrument is inserted into the body through the channel of a not shown trocar. After insertion, the jaws of clamp 4 are opened and, by way of illustration, an artery is cut off. Subsequently, the hook-and-eye connection is disconnected and the introduction and control component is removed.

In order to remove the clamp, exactly the reverse is done: first the hook 3 of the introduction component is reattached to the eye 53. The jaws of clamp 4 are opened by moving the rod 12.

After removal of the clamp 4, its jaws are closed again in such a manner that it can be taken out through the channel of the trocar.

Furthermore, in the shown preferred embodiment, the connection clamp/introduction component becomes rigid during insertion into and removal from the cavity by (partial) withdrawal into the tube 11.

Figure 2:
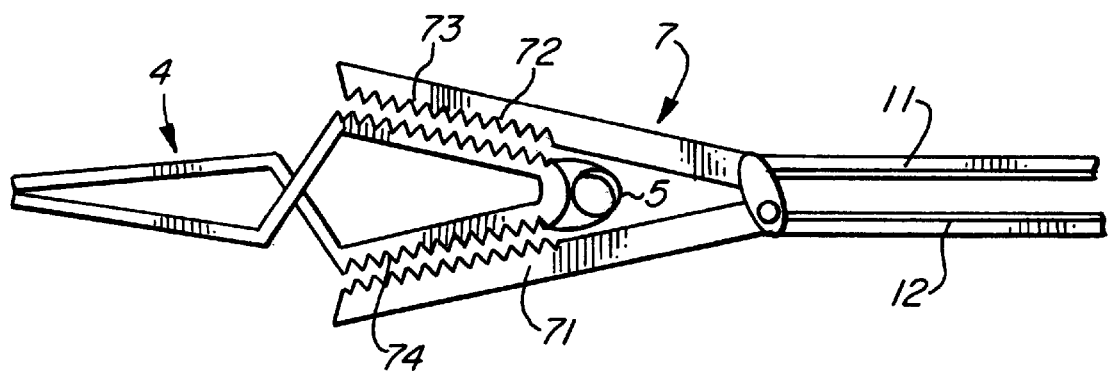
FIG. 2 shows a modification of the first preferred embodiment.

In FIGS. 2 and 3, the same or corresponding parts bear the same reference numbers, therefore obviating renewed presentation, and only deviations of the preferred embodiment shown in these figures from the first preferred embodiment are explained:

FIG. 2 shows a modification of the first embodiment, in which the connecting mechanism is not designed as a hook-and-eye connection. But rather, the connecting mechanism is provided with a pair of tongs 7 disposed on the rod-shaped component 1. The tong jaws formed by tong elements 71 and 72 can be opened and closed by operating the operator component 2. The tong elements 71 and 72 have the same toothing 73 on their gripping surfaces as the to be gripped surface 74 of the bulldog clamp 4, which is executed as one piece in the shown modification. The toothing 73 is designed as squares, the individual teeth of which are designed pyramid-shaped. Instead of the depicted spring 5, the bulldog clamp can also have a torsion spring.

FIGS. 3a and 3b show a second preferred embodiment, in which the distal part of the instrument, thus the operating element is a retractor, which by way of illustration can be employed like a liver retractor. The retractor is composed of an elastic wire cage 6, of which for the sake of simplicity only two "wires" are shown in FIG. 2b and which normally has the form shown by the solid lines in FIG. 3b. The wire cage 6 is closed by being drawn into the tube 11 of the introduction component (dashed lines) in such a manner that it can be led through the channel of a trocar or the like. After insertion of the retractor 6, the latter is pushed forward out of the tube 11 by the rod 12 of the introduction component in such a manner that that cage 6 unfolds. Subsequently the hook-and-eye connection is disconnected and the introduction component shown in FIG. 3a is removed again. The removal of the retractor runs exactly in reverse.

In the preceding the present invention has been described using preferred embodiments without the intention of limiting the scope or spirit of the overall inventive idea as can be drawn from the claims.

What is claimed is:

1. An instrument for use in endoscopic surgery in human or animal bodies, said instrument being insertable into said body through a channel of an insertion instrument, said instrument comprising:
   at least one operating element disposed at a distal end thereof;
   an introduction and control component connecting said operating element to a proximal region, said operating element and said introduction and control component being joined in such a manner via a connecting mechanism that said operating element can be disconnected intracorporally from said introduction and control component and can be reconnected thereto;

wherein said introduction and control component comprises a rod-shaped component which can be inserted into the channel of the insertion instrument, and a proximal operator component; and wherein said connecting mechanism is provided with a pair of tongs disposed on said introduction and control component, the jaws of said tongs capable of being opened and closed by operating the operator component and the tong elements of which include toothing which are sized and shaped to engage toothing provided on to be gripped surfaces of said operating element.

2. An instrument according to claim 1 wherein said operating element comprises a clamp which is closed in a non-operated state.

3. An instrument according to claim 1 wherein said toothing is designed as squares the individual teeth of which are designed pyramid-shaped.

4. An instrument according to claim 1 wherein said connecting mechanism is able to transfer at least axial tension and pressure forces onto said operating element.

5. An instrument according to claim 1 wherein said connecting mechanism is provided with a safeguard against accidental disconnection of the connection.

6. An instrument according to claim 1 wherein said operating element becomes more rigid by withdrawing into said introduction component.

7. An instrument according to claim 1 wherein by said operating element comprises a retractor.

8. An instrument according to claim 1 wherein said retractor is closed by being drawn into said introduction component.

9. An instrument according to claim 7 wherein said retractor comprises a liver retractor.

10. An instrument for use in endoscopic surgery in human or animal bodies, said instrument being insertable into said body through a channel of an insertion instrument, said instrument comprising:

at least one operating element disposed at a distal end thereof;

an introduction and control component connecting said operating element to a proximal region, said operating element and said introduction and control component being joined in such a manner via a connecting mechanism that said operating element can be disconnected intracorporally from said introduction and control component and can be reconnected thereto;

wherein said introduction and control component comprises a rod-shaped component which can be inserted into the channel of the insertion instrument, and a proximal operator component; and wherein said connecting mechanism comprises a hook-and-eye keyhole connection.

11. An instrument according to claim 10 wherein said introduction and control component comprising a cylindrical tube and a rod, which can be moved in the tube in direction of its longitudinal axis and bears said hook at its distal end.

12. An instrument according to claim 10 wherein said operating element comprises a clamp which is closed in a non-operated state.

13. An instrument according to claim 10 wherein said connecting mechanism is able to transfer at least axial tension and pressure forces onto said operating element.

14. An instrument according to claim 10 wherein said connecting mechanism is provided with a safeguard against accidental disconnection of the connection.

15. An instrument according to claim 10 wherein said operating element becomes more rigid by withdrawing into said introduction component.

16. An instrument according to claim 10 wherein by said operating element comprises a ratractor.

17. An instrument according to claim 16 wherein said retractor is closed by being drawn into said introduction component.

18. An instrument according to claim 16 wherein said retractor comprises a liver reactor.

* * * * *